(12) United States Patent
Ichizawa et al.

(10) Patent No.: US 8,823,819 B2
(45) Date of Patent: Sep. 2, 2014

(54) APPARATUS FOR MEASURING POSITION AND SHAPE OF PATTERN FORMED ON SHEET

(75) Inventors: Yasushi Ichizawa, Musashino (JP); Naomichi Chida, Musashino (JP); Minoru Akutsu, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 316 days.

(21) Appl. No.: 13/240,535

(22) Filed: Sep. 22, 2011

(65) Prior Publication Data
US 2012/0081539 A1 Apr. 5, 2012

(30) Foreign Application Priority Data
Sep. 30, 2010 (JP) .................. 2010-220307

(51) Int. Cl.
*H04N 5/225* (2006.01)
*H04N 7/18* (2006.01)
*G01N 21/89* (2006.01)

(52) U.S. Cl.
CPC ........... *G01N 21/8903* (2013.01); *H04N 5/225* (2013.01); *H04N 7/18* (2013.01)
USPC ......................................... 348/218.1; 348/95

(58) Field of Classification Search
None
See application file for complete search history.

(56) References Cited

U.S. PATENT DOCUMENTS

| | | | | |
|---|---|---|---|---|
| 5,144,132 A | * | 9/1992 | Kitakado | 250/208.1 |
| 5,380,978 A | * | 1/1995 | Pryor | 219/121.64 |
| 6,459,481 B1 | * | 10/2002 | Schaack | 356/241.1 |
| 2001/0014221 A1 | * | 8/2001 | Tomita | 396/325 |
| 2002/0175994 A1 | * | 11/2002 | Sakakibara et al. | 348/135 |
| 2003/0031384 A1 | * | 2/2003 | Zink | 382/293 |
| 2003/0183330 A1 | * | 10/2003 | Iseki et al. | 156/256 |
| 2004/0246497 A1 | * | 12/2004 | Chambard et al. | 356/612 |
| 2005/0046703 A1 | * | 3/2005 | Cutler | 348/223.1 |
| 2006/0033813 A1 | * | 2/2006 | Provinsal et al. | 348/143 |
| 2007/0037078 A1 | * | 2/2007 | Lee et al. | 430/30 |
| 2010/0295948 A1 | * | 11/2010 | Xie et al. | 348/175 |
| 2010/0309482 A1 | * | 12/2010 | Oikaze et al. | 356/601 |
| 2011/0069189 A1 | * | 3/2011 | Venkataraman et al. | 348/218.1 |
| 2011/0102596 A1 | * | 5/2011 | Kotani | 348/159 |

FOREIGN PATENT DOCUMENTS

| | | | | |
|---|---|---|---|---|
| JP | 04-085677 A | 3/1992 | | |
| JP | 2002-005846 A | 1/2002 | | |
| JP | 2002-042789 A | 2/2002 | | |
| JP | 2002221550 A | * | 8/2002 | ............ G01R 31/02 |
| JP | 2004-148534 A | 5/2004 | | |
| JP | 2007-041244 A | 2/2007 | | |

OTHER PUBLICATIONS

Japanese Office Action dated Sep. 13, 2012, issued in corresponding Japanese Patent Application No. 2010-220307 (2 pages).

* cited by examiner

*Primary Examiner* — Joseph Ustaris
*Assistant Examiner* — Edemio Navas, Jr.
(74) *Attorney, Agent, or Firm* — Westerman, Hattori, Daniels & Adrian, LLP

(57) ABSTRACT

An apparatus for measuring the position and shape of a pattern formed on a sheet includes a sheet on which a pattern is formed, a camera holding mechanism that is disposed perpendicular to a transportation direction of the sheet, at least one camera that is disposed such that the camera is movable in a longitudinal direction of the camera holding mechanism, and an image processing computer that processes an image picked up by the at least one camera. In the measuring apparatus, when calibration is performed, calibration is performed with reference to a picked up image of the coating pattern and a picked up image of a reference body for calibration.

4 Claims, 7 Drawing Sheets

APPARATUS FOR MEASURING POSITION AND SHAPE OF PATTERN FORMED ON SHEET

The present application is based upon and claims the benefit of priority from the prior Japanese Patent Application No. 2010-220307, filed on Sep. 30, 2010, the entire contents of which are incorporated herein by reference.

BACKGROUND OF THE INVENTION

1. Field of the Invention

The present disclosure relates to an apparatus for measuring the position and shape of a pattern that is formed on, for example, a sheet-shaped base material by coating or printing.

2. Description of the Related Art

In processes of manufacturing, for example, electrodes for capacitors or batteries, materials (coating substances) that realize specific electrical properties are applied to sheet base materials (simply referred to as sheets hereinafter). In this case, the coating substance is sometimes applied over the entire surface of a sheet. However, when the coating substance is expensive or the edge surfaces of the sheet need be free of the coating substance, only specified portions of the sheet are coated.

Such coating is referred to as partial coating, block coating, pattern coating, or the like.

To perform such coating, dimensions (width and length) of portions to be subject to coating are measured. When both surfaces of the sheet are to be coated, dimensional offsets (width and length) of the coating portions between the top and bottom surfaces also need be measured and controlled.

FIG. 6 is a conceptual diagram illustrating an example of a related-art coating pattern measuring apparatus using cameras for measurement. In FIG. 6, the sheet 1 is supported by transport rollers (not shown) and transported on a coating line at a constant speed. A plurality of cameras 31 (two cameras 31 in FIG. 6), to which lenses 30 are attached, are disposed on the coating line so as to measure coating dimensions.

In order to measure dimensions on the sheet 1, since the sheet moves at a constant speed, the cameras 31 need not have two-dimensional information. For this reason, line sensor cameras are widely used. In the line sensor camera, sensors as image pickup elements are arranged along a line perpendicular to a sheet moving direction. It is clear that an area sensor camera, which has two-dimensional information in image pickup elements, may instead be used. The sheet 1 includes coating portions 32 and portions to be observed 33.

For such a coating dimension measuring system, the following capabilities are required:

1. Resistance to Effects from Pass Line Variation

The sheet 1 is ideally transported at the same position on a transport line. In this case, the position where the sheet 1 passes through is referred to as a pass line. However, the sheet 1 does not actually pass through the completely same position in part of the coating line, but passes through vertically or laterally varied positions. For example, in a portion between the transport rollers and the like, where any support is not provided, the sheet 1 may vertically vibrate (a pass line variation). It is highly desirable that measurement of coating dimensions is free of that positional variation.

2. Flexible Accommodation of Coating Patterns

In FIG. 6, the sheet 1 has one coating pattern in a width direction thereof (single-row coating). Alternatively, a plurality of coating patterns may be formed in the sheet width direction. For example, two coating patterns may be formed in the sheet width direction (double-row coating). In this case, three cameras are required for picking up images.

Furthermore, three or four rows of coating patterns may be arranged in the width direction. For such cases, it is desirable that image pickup can be performed over the entire width of the sheet 1.

3. Size Reduction

Since the size of the coating line directly affects production costs, the size of the coating line is desirably reduced as much as possible.

Japanese Unexamined Patent Application Publications No. 2002-42789 and No. 2004-148534 are examples of related art.

SUMMARY OF THE INVENTION

When measuring the sheet width using the cameras 31 illustrated in an example of the related-art in FIG. 6, using ordinary lenses 30 causes the following problem. That is, a vertical variation (a change in the optical axis direction) of the coating line changes the size of images formed on the image pickup elements of the cameras 31.

FIG. 7A illustrates the state of the above-described situation. Since, in the ordinary lens 30, a principal ray passes through the center of the lens, an image of a measurement target A is focused at B as illustrated in FIG. 7A. When the measurement target approaches the lens 30 and reaches a position A', the principal ray still passes through the center of the lens 30. Thus, the image of A' is focused at B'.

In FIGS. 7A, B and B' are illustrated at horizontally shifted positions for explanatory purposes. Actually, both of B and B' are located on the image pickup elements at the same position. As can be seen from FIG. 7A, B' is a larger image than B. That is, when the sheet 1 to be measured moves from A to A' due to a variation in the optical axis direction, the size of an image is changed. This prevents correct measurement of the dimensions.

Even when a lens such as an above-described lens 30 is used, by reducing the angle of field of the lens 30, effects caused by the variation in the optical axis direction can be reduced.

FIG. 7B illustrates a state of image focusing when the angle of field of the lens 30 is reduced. As illustrated in FIG. 7B, the image of the measurement target A is focused at B. When the target approaches the lens 30 and reaches a position A', the principal ray still passes through the center of the lens 30. Thus, the image of A' is focused at B'.

In FIGS. 7A and 7B, B and B' are illustrated at horizontally shifted positions for explanatory purposes. Actually, both of B and B' are located on the image pickup elements at the same position. As can be seen from FIG. 7B, B' is a larger image than B. However, compared to the case illustrated in FIG. 7A, the ratio of the change is decreased in FIG. 7B. Although movement of the sheet 1 to be measured from A to A' slightly changes the size of the image, effects produced by this change are smaller than those in the case where the field of angle is larger. Thus, errors in dimensions can be reduced.

However, when the field of angle is reduced, an area inspected by one camera is reduced. When the cost is considered, it is difficult to pick up images over the entire width of the sheet.

Thus, the cameras are typically disposed at positions where the cameras can pick up portions to be observed such as edges of the sheet and ends of coating.

Today, coating technologies are widely used in manufacturing components and materials for secondary batteries and electronic components. Along with the increase in the use of coating, there are a variety of sheet widths and a variety of numbers of rows of coating materials on the sheets. In these cases, positions and numbers of images to be picked up by cameras may vary. With the above-described technology, there is a problem in that, when positions or the numbers of images to be picked up are changed, the measuring apparatus needs be replaced or modified to accommodate the change.

Accordingly, an object of the present application is to provide an apparatus for measuring the position and shape of a pattern formed on a sheet as follows. That is, with this measuring apparatus, in inspecting a width and a length of a coating pattern with cameras, a need for replacement or modification of the measuring apparatus is substantially eliminated even when there is a change in the number and positions of images to be picked up caused by a change in the width of the sheet or the number of rows of a coating material applied on the sheet in the width direction. In this case, high flexibility of the measuring apparatus is achieved at a low cost, and calibration performed in measuring a position and shape is simplified.

The present disclosure is proposed in part, in order to solve the above described problem. According to an aspect of the present disclosure, an apparatus for measuring a position and shape of a pattern formed on a sheet includes a sheet on which a pattern is formed, a camera holding mechanism that is disposed perpendicular to a transportation direction of the sheet, at least one camera that is disposed such that the camera is movable in a longitudinal direction of the camera holding mechanism, and an image processing computer that processes an image picked up by the at least one camera. In the measuring apparatus, when calibration is performed, calibration is performed with reference to a picked up image of the coating pattern and a picked up image of a reference body for calibration.

Preferably, the reference body for calibration is disposed at a position that is an image pickup position of the at least one camera having been moved by rotating the camera holding mechanism in the measuring apparatus.

In this case, the image of the position and the shape of a coating portion and the image of the reference body for calibration can be suitably compared, and accordingly, errors in measurement due to deviations in mechanical dimensions of a camera system can be minimized.

Preferably, the measuring apparatus further includes a mirror that is disposed away from the sheet by a specified distance. In the measuring apparatus, the reference body for calibration is disposed at a specified position in a mirror reflection direction within an image pickup range of the at least one camera that picks up an image of the sheet.

Preferably, the measuring apparatus further includes at least one laser light source that emits laser light toward the sheet. The at least one laser light source is disposed in the camera holding mechanism. In the measuring apparatus, the reference body for calibration is a laser spot formed by the laser light emitted from the at least one laser light source.

In this case, mirror is provided in the field of view of the camera, thereby including the reference body for calibration in the field of view together with the coating portion, and light such as laser light is emitted so as to project a dimensional reference position on the sheet to be measured, thereby comparing the projected reference position with the coating portion. This eliminates a need for a moving mechanism for the camera system, and accordingly, prevents generation of dust, occurrence of problems related to the life, and other problems occurring due to the moving mechanism.

Preferably, at least one camera includes a plurality of cameras spaced apart from each other at intervals of a specified distance in the camera holding mechanism. In the measuring apparatus, the plurality of cameras are movably secured to the camera holding mechanism in a longitudinal direction of the camera holding mechanism.

In this case, the cameras can be arbitrarily moved to positions corresponding to measurement targets in accordance with the number of rows of coating. Thus, there is no need for arranging the number of cameras sufficient to cover the entire width of coating, and accordingly, the numbers of cameras, the size of the image input board, and the like can be minimized, thereby realizing manufacture of the apparatus at a low cost.

Preferably, the sheet is an electrode of a battery.

BRIEF DESCRIPTION OF THE DRAWINGS

FIGS. 2A to 2D are diagrams for explaining a state of an image pickup screen when a camera holding mechanism illustrated in FIG. 1A is rotated;

FIGS. 4A to 4D are diagrams for explaining a state of an image pickup screen when the measuring apparatus illustrated in FIGS. 3A and 3B is used;

DESCRIPTION OF THE PREFERRED EMBODIMENTS

Figure 1A:
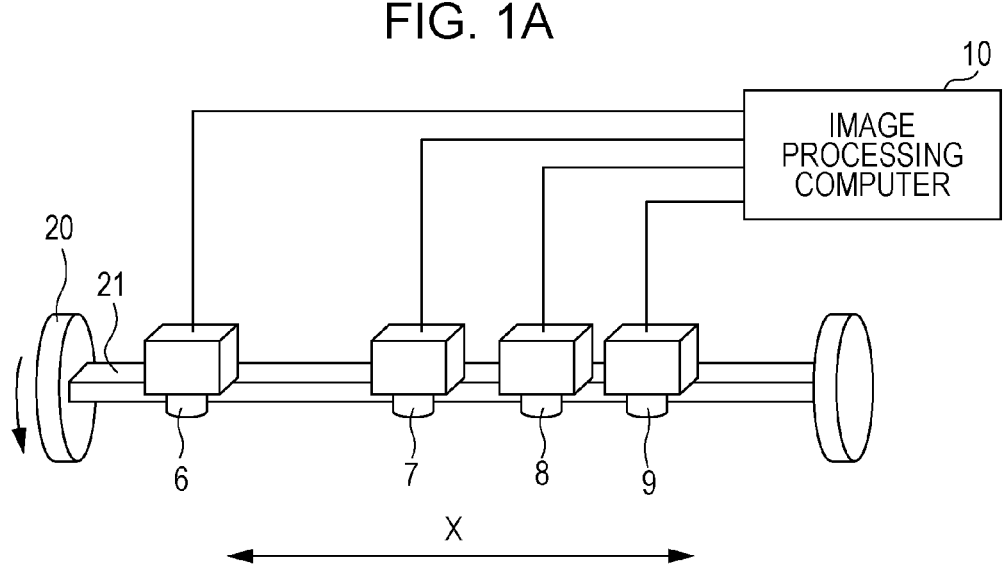
FIGS. 1A and 1B are schematic diagrams illustrating an apparatus for measuring the position and shape of a coating pattern as an example of an embodiment according to the present disclosure.
Figure 1B:
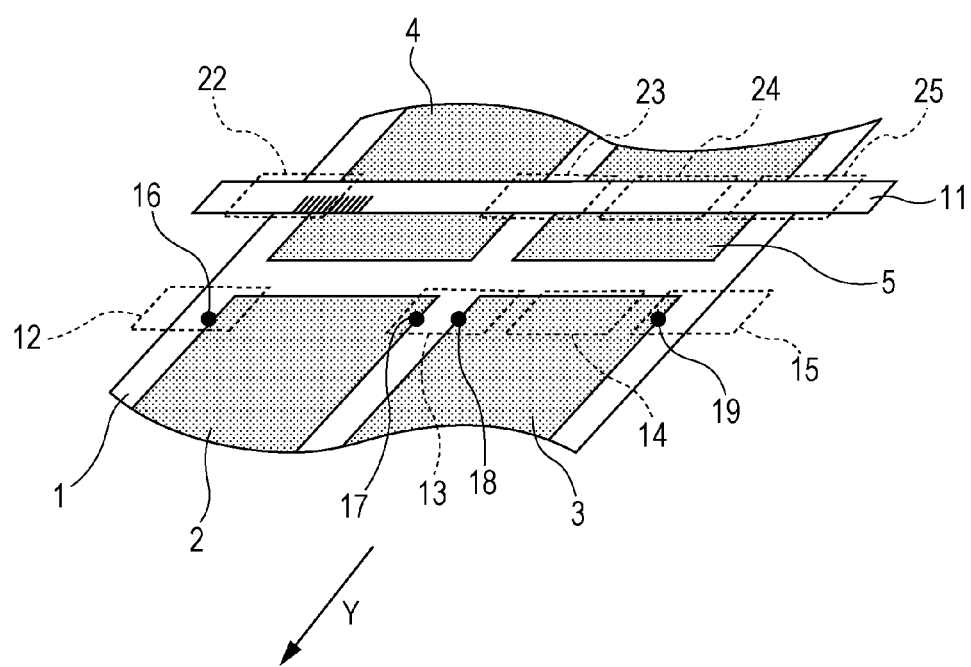

The present disclosure will be described below in detail with reference to the drawings. FIGS. 1A and 1B are schematic diagrams illustrating an apparatus for measuring the position and shape of a coating pattern as an example of an embodiment according to the present invention.

Referring to FIG. 1B, coating patterns 2 to 5 are coated on a sheet 1. The sheet 1 is transported on a conveyor (not shown) from the rear side to the front side of the drawing sheet at a constant speed.

FIGS. 2A to 2D are diagrams for explaining a state of an image pickup screen when a camera holding mechanism 21 illustrated in FIG. 1A is rotated through θ degrees toward the upstream of a flow of the sheet 1.

In these drawings, the camera holding mechanism 21 is disposed in a direction perpendicular to (an arrow X direction) a direction of the flow of the sheet 1 (an arrow Y direction). In the camera holding mechanism 21, four cameras 6 to 9 are linearly spaced apart in a longitudinal direction of the camera holding mechanism 21 at intervals of a specified distance.

A reference body for calibration (hereinafter referred to as a calibration scale) 11 is disposed near an image pickup portion on the sheet 1. The calibration scale 11 is held at a specified position on the sheet 1 using a holding mechanism (not shown).

Image pickup ranges of the cameras 6 to 9 are respectively portions 12 to 15, which are width measuring positions on the sheet 1. Although the cameras are secured to the camera holding mechanism 21, each of the cameras can be longitudinally moved to and secured to any positions on the camera holding mechanism 21.

Figure 2A:
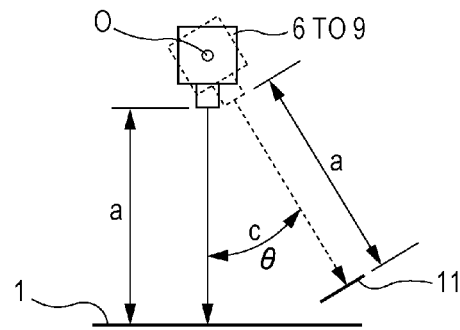
Figure 2C:
Figure 2C:
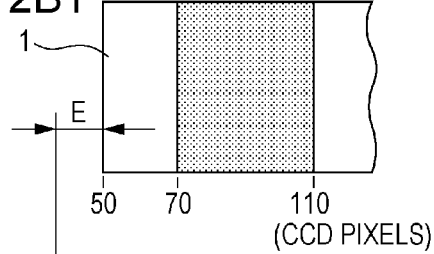
Figure 2C:
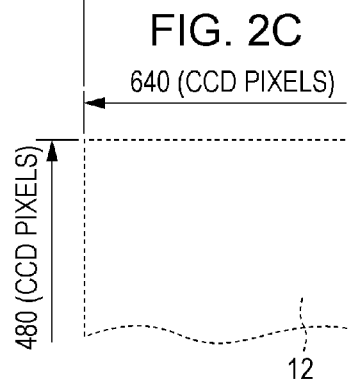

As illustrated in FIG. 2A, the camera holding mechanism 21 can be rotated using a rotation mechanism 20 in a direction indicated by an arrow c by θ degrees with the cameras 6 to 9 secured thereto.

The cameras 6 to 9 pick up images in image pickup ranges 22 to 25 during calibration. Running states of the measuring apparatus include an operation state and a calibration state. In the operation state, an image processing computer 10 observes the width measuring positions 12 to 19 on the sheet 1 using obtained video signals, and then performs image processing in order to calculate a distance between the edge of the sheet 1 and a coating portion, a distance between the coating portions, and the like. Inspection results obtained using the image processing computer 10 are then transmitted to a production control computer (not shown), or used to generate an alarm when a measured dimension is out of a reference dimensional ranges.

In the calibration state, the camera holding mechanism 21 is rotated using the rotation mechanism 20 about the rotation axis O in the arrow c direction by θ degree such that the cameras 6 to 9 pick up images in the image pickup ranges 22 to 25, respectively, while the relative positions of the cameras 6 to 9 are fixed. A focusing condition of the cameras 6 to 9 is specified between the sheet 1 and each of the cameras 6 to 9 in the operation state, and specified between the calibration scale 11 and each of the cameras 6 to 9 in the calibration state. Each involved element is set such that each of the cameras 6 to 9 operates under the same focusing condition (object distance a) in both of the states.

Calibration is performed in the following procedure:

1. The cameras 6 to 9 are secured such that the cameras 6 to 9 can pick up images of desired portions of the coated sheet 1.

2. The cameras 6 to 9 pick up images of the calibration scale 11 in order to create a dimension table in which the CCDs of the cameras and corresponding actual dimensions are listed.

3. Images of the coated sheet 1 are picked up and dimensions are calculated using the dimension table created above in 2.

FIGS. 2B1, 2B2, and 2C illustrate image pickup ranges of the cameras 6 to 9. A portion illustrated in FIG. 2B1 is an image of part of the sheet 1, and a portion illustrated in FIG. 2B2 is an image of part of the calibration scale 11. In the present embodiment, the number of pixels of each of the cameras 6 to 9 is 640×480 CCDs. Here, a margin E is set between the left edge of the image pickup range of a corresponding one of the cameras 6 to 9 and the edge of the sheet 1. The sheet 1 serving as a coating base starts at a position of 50 CCDs, which corresponds to the 102 mm marking on the calibration scale 11. The coating is formed in a range from 70 to 110 CCDs, which corresponds to a range from 115 to 139 mm markings on the calibration scale 11.

Figure 2D:
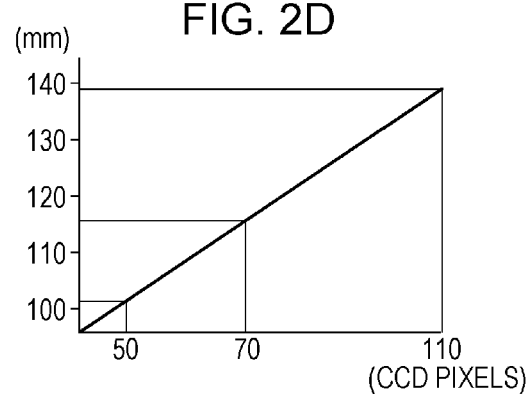

FIG. 2D illustrates the dimension table in which the scale widths are indicated in the vertical axis and the numbers of pixels are indicated in the horizontal axis.

In FIGS. 1A and 1B, the sheet 1 has two coating rows (coating rows in the width direction). Assume that the coating patterns 2 and 4 are collectively referred to as a first row and the coating patterns 3 and 5 are collectively referred to as a second row. When the number of rows becomes three, coating patterns of a third row are added on the right side of the second row. In this case, when the width of the sheet 1 is unchanged, the width of each coating pattern becomes smaller, and an additional image in a portion between the second and third rows needs to be picked up.

With the related art, it would be necessary that the measuring apparatus is replaced, or the measuring apparatus is modified in such a case.

In the measuring apparatus according to the present embodiment, positions of the cameras 6 to 9 are freely selectable on the camera holding mechanism 21 in the longitudinal direction. Thus, a change in image pickup positions can be accommodated by, for example, moving the camera 7 to a position between the first and second rows and the camera 8 to a position between the second and third rows.

By doing this, the positions at which the images are taken by the cameras 6 to 9 are changed, and accordingly, the relationships between the pixels of each of the cameras 6 to 9 and the dimensions on the sheet 1 used before the change in camera positions are changed. To accommodate this change, the camera holding mechanism 21 is moved to enter the calibration state using the rotation mechanism 20 in order to calibrate the relationships between the pixels of each of the cameras 6 to 9 and the dimensions. Thus, even when the positions of the cameras 6 to 9 are moved, calibration of the relationships between the pixels of each of the cameras 6 to 9 and the dimensions on the sheet 1 can be completed in a short time and the operation of the measuring apparatus can be started.

FIGS. 3A to 4D illustrate another embodiment. The differences between the embodiment illustrated in FIGS. 1A to 2D and this embodiment are as follows. That is, the rotation mechanism 20 provided in the measuring apparatus illustrated in FIGS. 1A to 2D is removed, a mirror 26 is added, and an angle at which the calibration scale 11 is held is changed.

The following description is dedicated to the difference in operation between the measuring apparatus illustrated in FIGS. 1A to 2D and the measuring apparatus illustrated in FIGS. 3A to 4D. Referring to FIGS. 3A to 4D, the mirror 26 is disposed at a position that splits the field of view of each of the cameras 6 to 9.

Figure 4A:
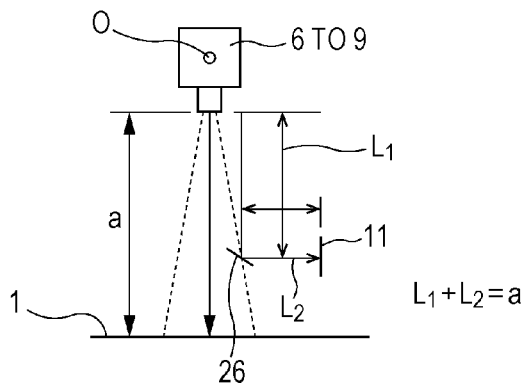

Referring to FIG. 4A, the sum of a distance L1 between the mirror 26 and each of the cameras 6 to 9 and a distance L2 between the mirror 26 and the calibration scale 11 is set to a distance equal to the distance a between each of the cameras 6 to 9 and the sheet 1. Thus, the image pickup range (field of view) of the camera 6 is set to the image pickup range 12 on the sheet 1 and the image pickup range 22 on the calibration scale 11. This setting of the image pickup ranges is similarly applied to the cameras 7 to 9.

Figure 4C:
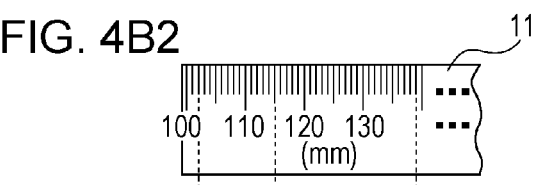
Figure 4C:
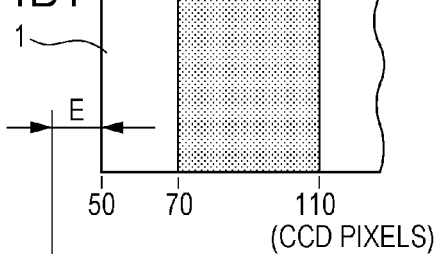
Figure 4C:
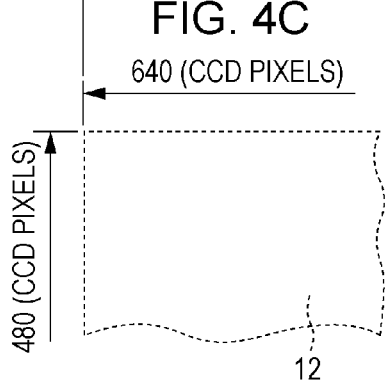
Figure 4D:
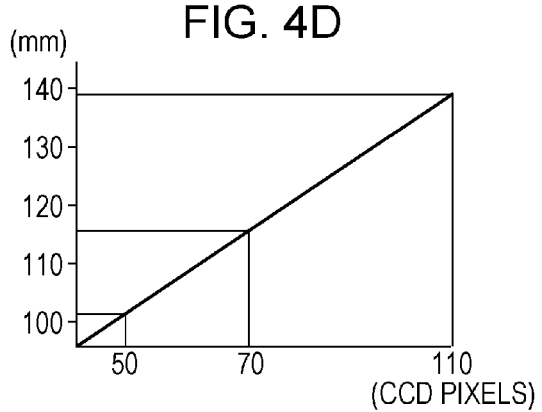

As illustrated in FIGS. 4B1 and 4B2, about a half of the area of an image (illustrated in FIG. 4B1) to be picked up by each of the cameras 6 to 9 is occupied by an image of part of the sheet 1, and the remaining about half of the area of the image (illustrated in FIG. 4B2) is occupied by an image of part of the calibration scale 11. By comparing the calibration scale 11 and the sheet 1 on a single image, the dimension of the coating portion on the sheet 1 can be measured. Similarly to FIGS. 2C and 2D, FIG. 4C illustrates the image pickup range, and FIG. 4D illustrates the scale widths in the vertical axis and the numbers of pixels in the horizontal axis.

In the embodiment illustrated in FIGS. 3A to 4D, images of the calibration scale 11 and the sheet 1 to be measured are simultaneously picked up by splitting the field of view. Thus, rotation of the camera holding mechanism 21 using the rotation mechanism 20, which is necessary for the measuring apparatus illustrated in FIGS. 1A and 1B, is not required. In addition, when the positions of the cameras 6 to 9 are moved so as to be aligned to the coating patterns, a calibration process is not required and the operation (measurement) can be immediately started.

Figure 3A:
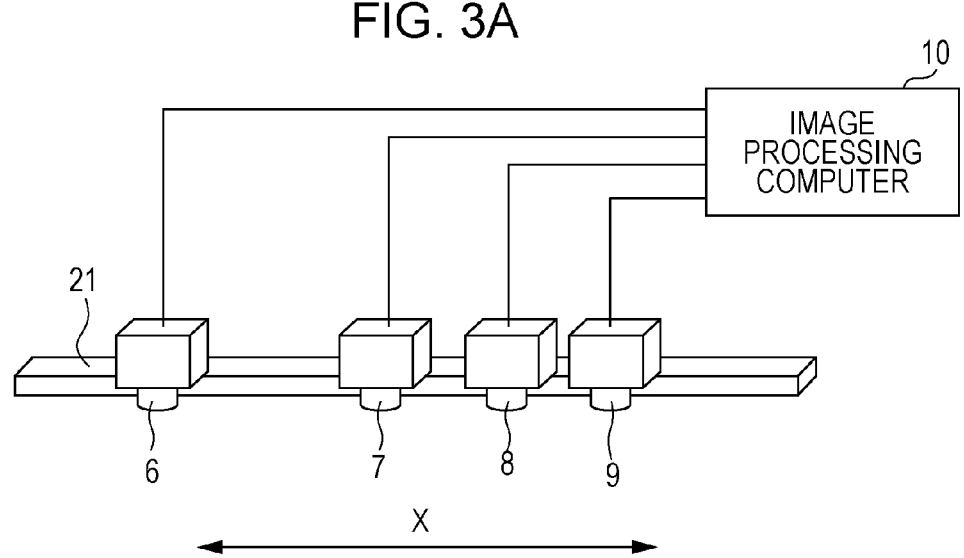
FIGS. 3A and 3B are schematic diagrams illustrating an apparatus for measuring the position and shape of a coating pattern as an example of another embodiment.
Figure 3B:
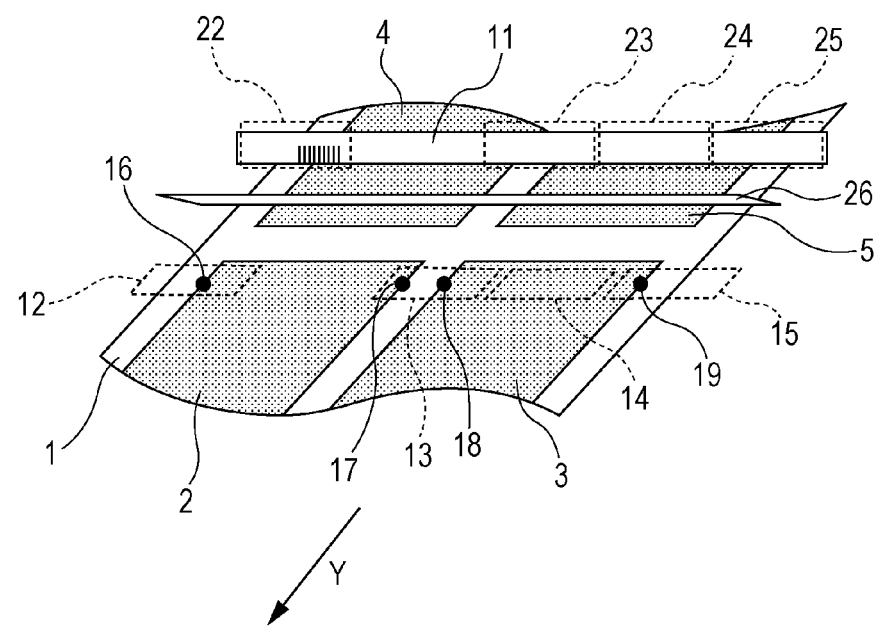

The angle and position of the mirror 26 are not limited to those illustrated in FIGS. 3A and 3B. For example, the mirror 26 may be mounted substantially perpendicular to the sheet flow direction at a substantially central position between the cameras 6 to 9 and the sheet 1. By doing this, the calibration scale 11 can be mounted on the camera holding mechanism 21.

Figure 5A:
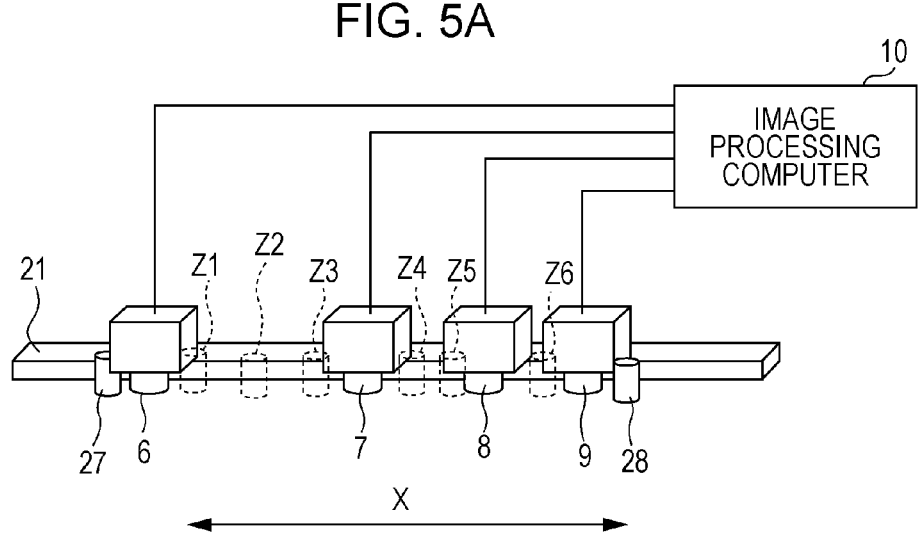
FIGS. 5A and 5B are schematic diagrams illustrating an apparatus for measuring the position and shape of a coating pattern as an example of yet another embodiment.
Figure 5B:
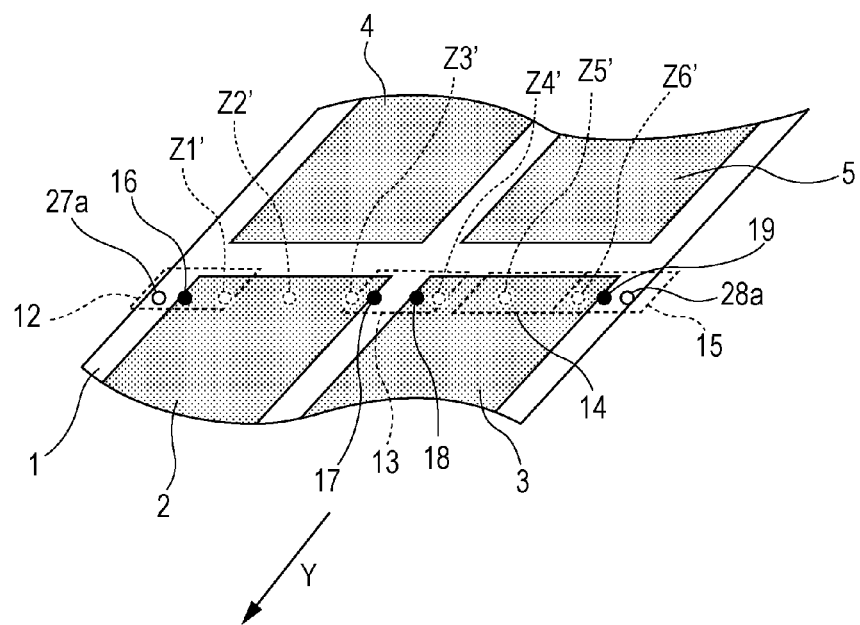
Figure 6:
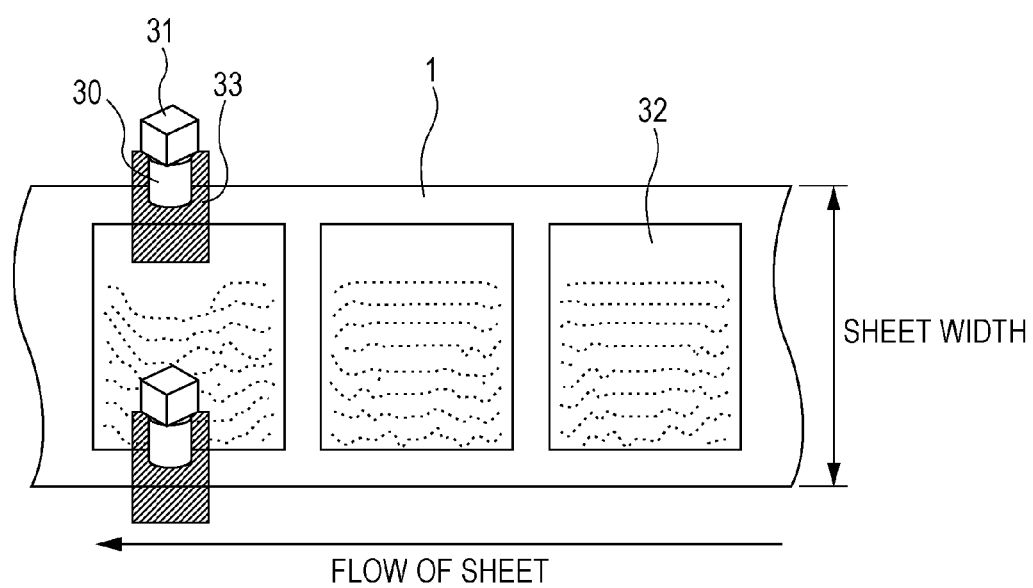
FIG. 6 is a conceptual diagram illustrating an example of a related-art coating pattern measuring apparatus.
Figure 7A:
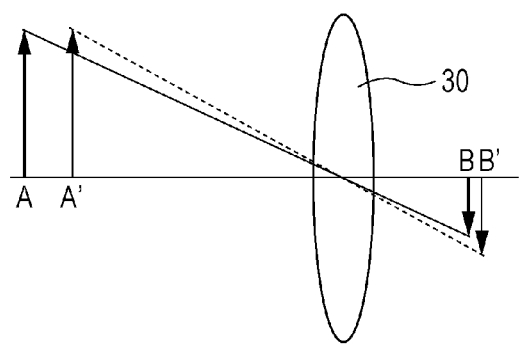
FIGS. 7A and 7B are diagrams explaining how sizes of images change when an ordinary lens is used.
Figure 7B:
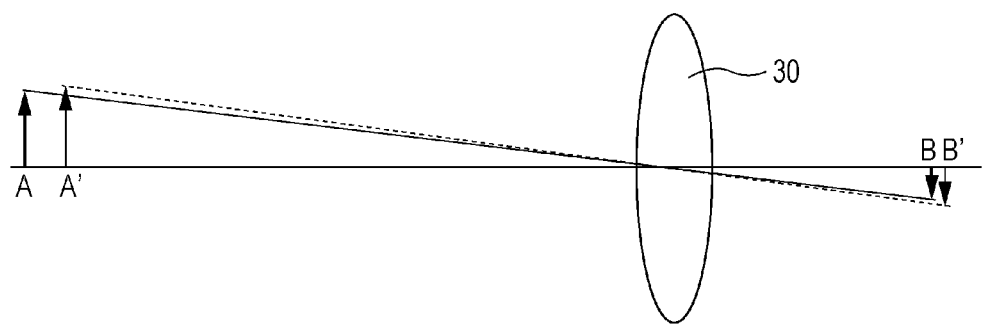

FIGS. 5A and 5B illustrate yet another embodiment. In this embodiment, laser light sources 27 and 28 are provided instead of the calibration scale 11 in a camera holding mechanism 21. The laser light sources 27 and 28 can emit spot-like patterns, projecting light so as to form equally spaced illumination spots 27a and 28a on the sheet 1.

In FIGS. 5A and 5B, although only the laser light sources 27 and 28 are illustrated, there are also laser light sources Z1 to Z6 drawn with dotted lines that project light so as to form illumination spots Z1' to Z6'.

A distance between the illumination spots 27a, 28a, and Z1' to Z6' is set to a length smaller than the field of view of each of the cameras 6 to 9, so that at least one of the illumination spots 27a, 28a, and Z1' to Z6' exists in the field of view of each of the cameras 6 to 9 even when the cameras 6 to 9 are moved to any position on the camera holding mechanism 21. In this case, the illumination spots 27a, 28a, and Z1' to Z6' are spots on the sheet 1, which indicate fixed dimensions as the calibration scale 11 indicates. Since the distances between the illumination spots 27a, 28a, and Z1' to Z6' and a particular position and the positions of these spots are known in advance, the illumination spots 27a, 28a, and Z1' to Z6' can be used instead of the calibration scale 11.

When the laser light emission is angled relative to the sheet 1 instead of perpendicular to the sheet 1, variations of the position of the sheet transport line in the light emitting direction may affect illumination positions. When the variations are not negligible, an arrangement of a plurality of light sources that each perpendicularly emit light, or the like is required.

The method of forming illumination spots equally spaced on the sheet 1 does not necessarily use laser light. A high intensity lamp, a film mask for projecting light, and the like may be used so as to project a pattern of the mask on the sheet 1.

The above description is only preferable specific embodiments for describing and exemplifying the present disclosure. For example, the number of cameras may be one or more, and a target formed on the sheet is not necessarily coated, but may be printed.

Accordingly, the present disclosure is not limited to the above embodiments, but further includes many changes and modifications without departing from the essentials of the present invention.

What is claimed is:

1. A coating pattern measuring apparatus for measuring a dimension of a coating portion formed on a sheet-shaped base material, the apparatus comprising:
    a camera holding mechanism that is disposed perpendicular to a transportation direction of the sheet-shaped base material;
    at least one camera that is held by the camera holding mechanism and is disposed such that the at least one camera is movable in a longitudinal direction of the camera holding mechanism;
    a rotation mechanism that rotates the camera holding mechanism by θ degrees to rotate the at least one camera from a first image pickup position at a first position at which the coating portion is formed on the sheet-shaped based material to a second image pickup position at a second position, wherein the at least one camera is focused at the same object distance at the first image pickup position and the second image pickup position;
    a scale for calibration that is disposed at the second image pickup position of the at least one camera and is disposed perpendicular to the transportation direction of the sheet-shaped base material and whose image can be picked up by the at least one camera, the scale for calibration extending across the entire width of the sheet-shaped base material and the scale for calibration not being disposed at the first image pickup position; and
    an image processing computer that processes an image picked up by the at least one camera,
    wherein the relationship between a pixel of the at least one camera and a position on the sheet-shaped base material is determined with reference to a picked up image of the scale for calibration.

2. A coating pattern measuring apparatus for measuring a dimension of a coating portion formed on a sheet-shaped base material, the apparatus comprising:
    a camera holding mechanism that is disposed perpendicular to a transportation direction of the sheet-shaped base material;
    at least one camera that is held by the camera holding mechanism and is disposed such that the at least one camera is movable in a longitudinal direction of the camera holding mechanism;
    a rotation mechanism that rotates the camera holding mechanism by θ degrees to rotate the at least one camera from a first image pickup position at a first position at which the coating portion is formed on the sheet-shaped based material to a second image pickup position at a second position, wherein the at least one camera is focused at the same object distance at the first image pickup position and the second image pickup position;
    a scale for calibration that is disposed at the second image pickup position of the at least one camera and is disposed perpendicular to the transportation direction of the sheet-shaped base material and whose image can be picked up by the at least one camera, the scale for calibration extending across the entire width of the sheet-shaped base material and the scale for calibration not being disposed at the first image pickup position; and
    an image processing computer that processes an image picked up by the at least one camera,
    wherein the relationship between the number of pixels of the at least one camera and a dimension on the sheet-shaped base material is determined with reference to a picked up image of the scale for calibration.

3. The coating pattern measuring apparatus for measuring a dimension of a coating portion formed on a sheet-shaped base material as recited in claim 1, wherein a plurality of the cameras are arranged so as to be spaced apart from each other at intervals of a specified distance in the camera holding mechanism, and the plurality of cameras are secured such that the cameras are movable in the longitudinal direction of the camera holding mechanism.

4. The coating pattern measuring apparatus for measuring a dimension of a coating portion formed on a sheet-shaped base material as recited in claim 2, wherein a plurality of the cameras are arranged so as to be spaced apart from each other at intervals of a specified distance in the camera holding mechanism, and the plurality of cameras are secured such that the cameras are movable in the longitudinal direction of the camera holding mechanism.

\* \* \* \* \*